United States Patent
Yousif et al.

(10) Patent No.: US 12,325,868 B2
(45) Date of Patent: Jun. 10, 2025

(54) PURIFIED FISH PROTEASES WITH HIGH SPECIFIC ACTIVITIES AND ITS PROCESS OF PRODUCTION

(71) Applicant: BIOSEUTICA B.V., Zeewolde (NL)

(72) Inventors: Alex Nobar Yousif, Coquitlam (CA); Priyanka Dutta Passecker, Waidhofen an der Ybbs (AT); Valerio Maria Ferrari, Milan (IT); Jay Siddharth, Bissone (CH)

(73) Assignee: BIOSEUTICA B.V., Zeewolde BD (NL)

( * ) Notice: Subject to any disclaimer, the term of this patent is extended or adjusted under 35 U.S.C. 154(b) by 720 days.

(21) Appl. No.: 17/595,093

(22) PCT Filed: Apr. 27, 2020

(86) PCT No.: PCT/EP2020/061588
§ 371 (c)(1),
(2) Date: Nov. 9, 2021

(87) PCT Pub. No.: WO2020/229145
PCT Pub. Date: Nov. 19, 2020

(65) Prior Publication Data
US 2022/0204922 A1 Jun. 30, 2022

Related U.S. Application Data

(60) Provisional application No. 62/847,013, filed on May 13, 2019.

(51) Int. Cl.
| | | |
|---|---|---|
| *C12N 9/64* | (2006.01) | |
| *B01D 15/32* | (2006.01) | |
| *B01D 15/42* | (2006.01) | |
| *B01D 61/14* | (2006.01) | |
| *B01D 61/24* | (2006.01) | |
| *B01D 61/58* | (2006.01) | |
| *B01D 69/02* | (2006.01) | |
| *C07K 1/20* | (2006.01) | |
| *C12N 5/071* | (2010.01) | |

(52) U.S. Cl.
CPC ......... *C12N 5/0602* (2013.01); *B01D 15/327* (2013.01); *B01D 15/426* (2013.01); *B01D 61/145* (2013.01); *B01D 61/243* (2013.01); *B01D 61/58* (2013.01); *B01D 69/02* (2013.01); *C07K 1/20* (2013.01); *C12N 9/6408* (2013.01); *C12Y 304/21001* (2013.01); *C12Y 304/21004* (2013.01); *B01D 2311/06* (2013.01); *B01D 2325/20* (2013.01)

(58) Field of Classification Search
CPC .. C12N 5/0602; C12N 9/6408; B01D 15/327; B01D 15/426; B01D 61/145; B01D 61/243; B01D 61/58; B01D 69/02; B01D 2311/06; B01D 2325/20; C07K 1/20; C12Y 304/21001; C12Y 304/21004
See application file for complete search history.

(56) References Cited

U.S. PATENT DOCUMENTS 7,070,953 B1 7/2006 Bjarnason et al.

FOREIGN PATENT DOCUMENTS

| EP | 3121272 A1 | 1/2017 |
|---|---|---|
| WO | 2000078332 A2 | 12/2000 |
| WO | 2011126957 A1 | 10/2011 |
| WO | 2015150799 A1 | 10/2015 |

OTHER PUBLICATIONS

A. Gudmundstottir et al., "Potential use of atlantic cod trypsin in biomedicine", Biomed Research International, vol. 2013, Jan. 1, 2013, pp. 1-11.
Asgeirsson B. et al., "Purification and characterization of trypsin from the poikilotherm gadus morhua", European Journal of Biochemistry, vol. 180, No. 85, May 1, 1989, pp. 85-94.
Hayet Ben Khaled et al., "Purification and characterization of three trypsin isoforms from viscera of sardinelle", Fish Physiology and Biochemistry, Kluwer Academic Publishers, DO, vol. 37, No. 1, Aug. 14, 2010, pp. 123-133.
Search Report and Written Opinion of PCT/EP2020/061588 of Jul. 22, 2020.
Stefansoon B et al., "Characterization of cold-adapted Atlantic cod (*Gadus morhua*) trypsin I—kinetic parameters, autolysis and thermal stability", Comparative Biochemistry and Physiology Part B: Biochemistry and Molecular Biology, Elsevier, Amesterdam, NL, vol. 155, No. 2, Feb. 1, 2010, pp. 186-194.

*Primary Examiner* — Satyendra K Singh
(74) *Attorney, Agent, or Firm* — Silvia Salvadori, P.C.; Silvia Salvadori

(57) ABSTRACT

The invention concerns a process for the preparation of fish proteases from fish viscera, preferably from cod (*Gadus* genus) viscera. The fish proteases produced according to the invention have high specific enzymatic activity and are useful for food uses, for biomedical applications, in histology and tissue culture.

9 Claims, 3 Drawing Sheets

Before　　　　　　　　　　　　　　After

Figure 1:
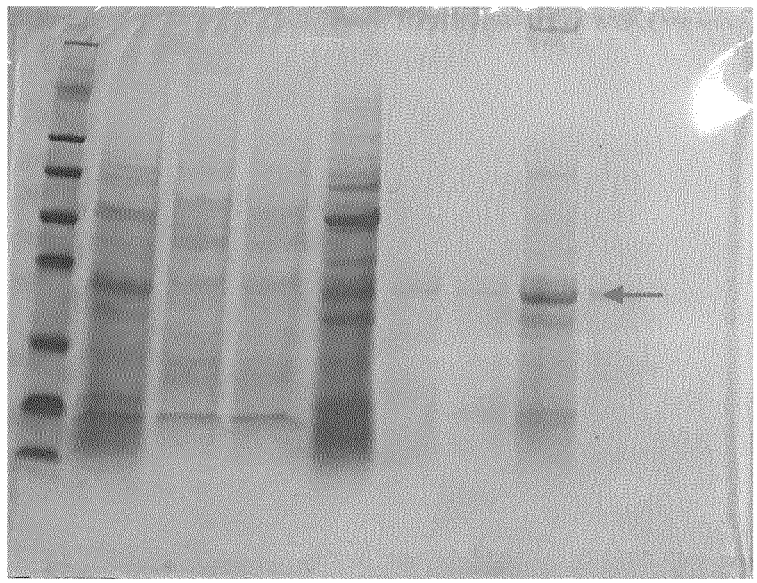

PURIFIED FISH PROTEASES WITH HIGH SPECIFIC ACTIVITIES AND ITS PROCESS OF PRODUCTION

This application is a U.S. national stage of PCT/EP2020/061588 filed on 27 Apr. 2020, which claims priority to and the benefit of U.S. Provisional Application No. 62/847,013 filed on 13 May 2019, the contents of which are incorporated herein by reference in their entireties.

FIELD OF THE INVENTION

The invention concerns a process for the preparation of fish proteases from fish viscera, preferably from cod (*Gadus* genus) viscera. The fish proteases produced according to the invention have high specific enzymatic activity and are useful for food uses, for biomedical applications, in histology and tissue culture.

BACKGROUND

The proteolytic activity of trypsin (EC 3.4.21.4) was first described in 1876 by W. Kuhne in pancreatic secretions ("Über das Trypsin (Enzym des Pankreas)", Verhandlungen des naturhistorisch-medicinischen Vereins zu Heidelberg, vol. 1, no. 3, pages 194-198).

This enzyme specifically hydrolyzes peptide bonds C-terminal to the amino acid residues of lysine and arginine about one hundred times faster than a basic hydrolysis. Since its initial discovery, trypsin has been identified in all animals, including insects, fish, and mammals. Trypsin from each source differs slightly in activity, but the natural substrate for the enzyme is any peptide that contains lysine or arginine.

Human trypsin hydrolyzes peptide bonds after arginine or lysine residues, its activity being optimal between pH 7.5 and 8.5 and in the presence of calcium ions; moreover, human trypsin has optimal operating temperature of about 37° C.

Fish trypsins, such as those isolated from Atlantic cod, have different optimal temperature ranges (as poikilotherm organisms like fish live at low body temperatures). For example, cod trypsins include trypsin I, having a maximal temperature activity range of 4 to 65° C. and maximal activity at 55° C., and trypsin Y having an activity range comprised between 2 and 30 C and a maximal activity at 21° C. (Gudmundsdóttir A et al., 2005 March-April; 7(2):77-88); Hindawi Publishing Corporation; BioMed Research International, Volume 2013, Article ID 749078). Another relevant difference between mammalian and fish trypsins is their thermal stability: for example, fish trypsins but not mammalian trypsins are completely inactivated by a pasteurization process. As a protein, trypsin shows various molecular weights depending on the source. For example, a molecular weight of 23.3 kDa is reported for trypsin from bovine and porcine sources, while fish trypsin I, trypsin X and trypsin Y, isolated from Atlantic cod, have molecular masses of 23.9 kDa, 23.9 kDa and 25.1 kDa, respectively (Bjarki Stefansson et al., Characterization of cold-adapted Atlantic cod (*Gadus morhua*) trypsin I—Kinetic parameters, autolysis and thermal stability; Comparative Biochemistry and Physiology, Part B; (2010) 186-194). The commercial applications of trypsins may include, inter alia, their use in the development of cell and tissue culture protocols (Soleimani M.; Nadri S. A, Nature protocols (2009), 4(1), 102-6), in the protein identification through peptide sequencing techniques (Schuchert-Shi et al., Analytical Biochemistry (2009), 387 (2), 202-207) and in the medical field to model the decomposition of articular cartilage in osteoarthritis (Wang S. et al., Connective tissue research (2010), 51(1), 36-47). Particularly fish trypsin (Atlantic cod trypsin I) has already proved its usefulness in a variety of industrial applications (Bjarnason, J. B. et al., Psychrophilic proteinases from Atlantic cod ACS Symposium Series (1993), 516 (Biocatalyst Design for Stability and Specificity), 68-82) including the production of an all-natural seafood flavour from lobster, shrimp, crab, and other seafood. More recently, cod trypsin has shown high efficacy in degradation of native proteins and in vitro anti-pathogenic efficacy against HSV-1 and RSV, opening new perspectives for new therapeutic uses of fish proteases (BioMed Research International Volume 2013, Article ID 749078). A critical aspect of the use of proteases, and also of marine trypsins, is their stability, as they undergo autolysis. For this reason, they should be stored at very low temperatures (between −20 and −80° C.) to prevent degradation. Autolysis may be controlled by keeping these proteases at pH 3 or by using proteases modified by reductive methylation. Serine proteases (a class of proteases which also include trypsin) show restored activity when the pH is adjusted back to pH 8, (F. M. Pohl European J. Biochem. 7 (1968), 146-152; Aizawa, N.; Yokohama Medical Bulletin (1960), 11, 101-10) although an important loss of activity when working under very alkaline conditions (pH 10) is described (B. K. Khangembam et al., International Aquatic Research, December 2012, 4:9). Commercially available marine proteases extracted from the gut of crustaceans, and identified by the CAS registry number 534583-22-7 (trade name Accutase), are also temperature sensitive: they are stable at 4° C. for 60 days but quickly lose 75% of their enzymatic activity (in 90 minutes) when stored at 37° C. The standardization of the characteristics of these purified trypsins and proteases, in terms of stability and enzymatic activities, is important in view of their commercial use, as they could be validated for use as production reagents (e.g. in the food chemistry) and in histology and tissue culture. The pyloric cecum of Atlantic cod, acting as a digestive organ, is a by-product of the fishing industry and can be utilized as a cheap starting material for the isolation of fish proteases, including trypsins. It is rich in digestive enzymes such as serine proteases (Asgeirsson B. et al., Eur J Biochem 180(1), 85-94).

The best known members of these serine protease family from Atlantic cod are trypsins, chymotrypsins, elastases, serine collagenases, and brachyurins (Halfon S, Craik C S (1998) "Family 51 of trypsin (clan SA)" In: Handbook of Proteolytic Enzymes, Barrett A J, Rawlings N D, Woessner J F, eds. (San Diego, Calif.: Academic Press) pp 5-12). In more detail, three native trypsin isozymes, termed trypsins I, II, and III, were isolated from the pyloric ceca of Atlantic cod. Trypsin I, the most abundant and best characterized form, also shows the highest catalytic efficiency which is approximately 20 times higher than that of its mesophilic bovine analogue. The known methods of purification of proteases from fish viscera (Comparative biochemistry and physiology. Part B, Biochemistry & molecular biology (1995), 110(4), 707-17; Journal of Agricultural and Food Chemistry, 39 (10), Pages 1738-42 (1991)) are however quite complex and require several purification steps which may include, inter alia, $(NH_4)_2SO_4$ fractionation and several chromatographic purifications, including hydrophobic interaction chromatography, affinity chromatography or ionic exchanged chromatography. It should be noted that, on the basis of the data reported in the literature, the global yields of purification of trypsin from the crude extracts are low and the obtained specific enzymatic activity is of a few Units/mg.

Moreover, the need to stabilize trypsins from autolysis during long purification process, working in the presence of $Ca^{2+}$ and at low temperature, implies high costs for the scaling up to an industrial scale. More simple and effective processes of purification are therefore required.

DESCRIPTION OF THE INVENTION

The invention provides a process for the purification of fish proteases from fish viscera, comprising:
- a) Extraction of crude enzyme from fish viscera with a calcium chloride buffer at pH 7, filtration and ultrafiltration;
- b) Extraction of the ultrafiltrate with an aqueous solution of $CaCl_2$ having conductivity 52 to 62 mS in a pH range of 7.8÷8.2 followed by depth filtration;
- c) Purification by hydrophobic interaction chromatography of the filtrate using as stationary phases an agarose base matrix with straight chain alkyl ligands or aryl ligands and eluted by elution with buffers of low salt content and then with an aqueous mixture of water miscible organic solvents and a polyol;
- d) Dialysis;
- e) Optional freeze-drying.

The proteases obtained by the process of the invention have an average specific Trypsin activity of 240 U/mg±40 U/mg, Chymotrypsin activity of 4±2 U/mg, Collagenase activity of 0.04±0.02 U/mg and a Protease activity of 65±10 U/mg.

The process provides overall yields of solid fish proteases of 0.06-0.11% by weight of the cod viscera used as starting material.

Fish viscera are preferably cod viscera.

The extraction process of step a) is carried out at a temperature between 4 and 25° C.

The pH calcium chloride buffer has preferably a final concentration of 20 mM.

The ultrafiltration is preferably carried out using a membrane with a 1 kDalton cut off whereas the agarose base matrix of the stationary phase used in step c) presents aryl ligands and a particle size distribution between 50 and 100 microns.

The chromatographic elution with buffers of low salt content in the step c) is preferably done using a 1.5 M aqueous sodium acetate solution, the water-miscible organic solvent is isopropanol and the polyol is glycerol.

Step c) is preferably carried out at a temperature between 4 and 25° C.

Detailed Description: Definitions

Cellular Lines Tested for the Detachment and Dissociation of Anchorage-Dependent Cells from Surfaces PC12 cells (a cell line derived from a pheochromocytoma of the rat adrenal medulla) appear to possess specific receptors and responses to epidermal growth factor (EGF) (Huff and Guroff, 1979). The presence of such receptors could reflect a hitherto unidentified role of EGF during neuronal development or could, alternatively, correlate with the neoplastic nature of PC12 cells. PC12 cells provide a model for studying chemical disruption of processes associated with neuronal differentiation, synthesis, storage and release of neurotransmitters, function and regulation of ion channels and interactions of compounds with membrane bound receptors.

Induced pluripotent stem cells (iPSC) are a type of pluripotent stem cell that can be generated directly from adult cells. These cells can be differentiated into the hepatic lineage and provide an accurate model for liver diseases, drug screening and drug toxicity testing (Curr Stem Cell Res Ther. 2015; 10(3):208-15).

Neuronal progenitor cells (NPC) are multipotent stem cells with the capability to differentiate into neurons and glial cells (oligodendrocytes and astrocytes). Therefore, successful in vitro neural progenitor cell expansion offers significant therapeutic potential for cell therapy applications.

Human bone osteosarcoma epithelial cells (U2OS) could satisfy the need for an in vivo metastatic model for osteosarcoma.

Enzymatic Tests Used

Trypsin activity. Enzymatic activity analyzed according to the method described in the USP 41 monograph.

Chymotrypsin activity. Enzymatic activity analyzed according to the method described in the USP 41 monograph.

Collagenase type I activity. Enzymatic activity analyzed according to protocols described in the literature (Mandl, I. J. Clin. Invest. 32, 1323. 1953. Moore, S. et al., J. Biol. Chem. 176, 367. 1948).

Protease activity. Enzymatic activity analyzed according to the method described in the USP 41 monograph.

The consistency of the claimed process was confirmed using different batches of cod viscera (caught at different times of the year) as starting material: the obtained fish proteases proved to have limited variability from batch to batch; this variability does not exceed the range of ±15% with respect to the obtained specific enzymatic activities.

The purified fish proteases prepared according to the process of the invention present a peculiar enzymatic profile: in fact, while commercially available marine trypsins (such as marine proteases identified by the CAS registry number 534583-22-7) show trypsin activity around 26-49% and collagenase type I activity around 47-67% of the total enzymatic activity, the fish proteases prepared according to the process of the invention show trypsin activity of about 89-66% of the total enzymatic activity, and a collagenase activity of only 0.011-0.015%.

Surprisingly, the fish proteases prepared according process of the invention when utilized in histology for cell detachment, are less harmful to cells than other marine proteases, leading to increased viability. In detail, when NPC and PC12 cell lines are treated with the fish proteases obtained according to the invention, the survival rate and the number of recovered cells is about 5-10% higher than other trypsins/proteases of mammalian and marine origin.

DETAILED DESCRIPTION: PROCESS

Frozen (−20° C.) cod viscera were thawed at 20-25° C., then combined with 20 mM calcium chloride dihydrate extraction buffer in a relative ratio of 1 kg of fish viscera for 2 L calcium chloride buffer. The resulting mixture was adjusted to a final pH 7 by addition of sodium hydroxide 50% w/v water solution of and stirred for 8-12 hours at 4° C.

Large viscera chunks were separated by filtration with a net (1 mm cut-off).

A filter aid was added to the obtained mixture, under stirring at 20-25° C., which was then filter pressed.

Suitable filter aids are diatomaceous earth, perlite, cellulose added in a amounts comprised between 3 and 7% by weight with respect to the volume of the mixture. Preferably diatomaceous earth is used in an amount of 5% w/v with respect to the mixture.

The filtered extract was concentrated by ultrafiltration (1 kDa cut off) to 42% of the initial volume and stored at 4° C. if not immediately used in the next purification process. The concentrated fish extract was warmed to 20-25° C. and calcium chloride dihydrate was added to reach a final concentration comprised between 1.0 and 1.8 w/v, preferably 1.4% w/v. Sodium acetate was added to reach a final concentration between 1.0 and 2.0 M, preferably 1.5 M, and the pH adjusted in a range between 7.8 and 8.2, preferably 8.0, using 5 M sodium hydroxide water solution.

The correct concentration of the salts is obtained, when the conductivity of the mixture is comprised in a range between 54 and 62 mS, preferably between 56 and 60 mS.

After stirring the mixture for one hour at 20-25° C., a filter aid was added and the obtained suspension filtered. Suitable filter aids are diatomaceous earth, perlite, cellulose added in an amount comprised between 1 and 4% by with weight respect to the volume of the mixture. Preferably diatomaceous earth is used in an amount of 2% w/v with respect to the mixture.

The obtained suspension is then filtered using a filter press equipped with suitable depth filters. The operative pressure used for this filtration is comprised between 50 and 70 psi, preferably 60 psi, and the suitable depth filters employed should have a cut off comprised between 6 and 9 microns. Preferred depth filters are cellulose filters sheets or rigid media filter contains porous metal, ceramic or plastic media. Preferably XE-400 filter sheets are used (Carlson filtration).

Then the obtained filtrate was purified by hydrophobic interaction chromatography (HIC): the ratio of the volume of the feed material to the volume of the used stationary phase is comprised between 4 and 8 volume/volume, preferably 6, 7. The preferred particle size of the stationary phase is comprised between 50 and 100 microns, preferably 75 microns. The stationary phases present an agarose base matrix with different immobilized ligands, such as straight chain alkyl ligands or aryl ligands. Preferred ligands are aryl ligands. The stationary phase prior use is washed with at least 3 bed volumes of 0.1 M sodium hydroxide aqueous solution and then with 3 bed volumes of distilled water. Then the column was conditioned with 4 BV with a solution prepared using a sodium acetate aqueous solution at a concentration comprised between 1.0 and 2.0 M, preferably 1.5 M, at a pH value comprised between 7.8 and 8.2, preferably 8.0, obtained by addition of a 5 M sodium hydroxide solution. The solution and the eluates are fed at $1/10$ ml/minute flow rate with respect to the total volume of the stationary phase and at a pressure comprised between 10 and 20 psi, preferably 15 psi. After the absorption, the bound solutes are eluted by stepwise or gradient elution with buffers with low salt content and then with an aqueous mixture of water miscible organic solvents and a polyol. Suitable water miscible organic solvents have a log P (hydrophobicity) comprised between −0.31 and +0.25, such as n-propanol, isopropanol and ethanol, preferably isopropanol. Suitable polyols are glycerol, ethylene glycol, ethylene glycol and sorbitol, preferably glycerol.

The elution is preferably effected under the following conditions: 2 bed volumes of 1.5 M sodium acetate at pH 8, then elution with 3 bed volumes of a solution of 10% v/v glycerol and 5% v/v isopropanol (diluted with distilled water). Eluates were collected in 4 fractions of about 1 bed volume each. The eluted fractions with trypsin activity were pooled together, concentrated to $1/10$ of the starting volume by ultrafiltration (using an ultrafiltration membrane with a cut off of 1 kDa). Then the concentrated solution was diluted under stirring to 1/2.2 with a 20 mM $CaCl_2$ aqueous solution at pH 8, dialyzed to restore the original volume then freeze dried to afford a purified fish protease. 33-60 g of purified fish proteases with an average Trypsin enzymatic activity of 240 U/mg, Chymotrypsin activity of 5 U/mg and a collagenase activity of 0.04 U/mg were recovered from 52 Kg of cod viscera. Optionally, the process of the invention can be stopped after the dialysis step (i.e. avoiding the final freeze drying step) to obtain fish proteases in aqueous solution useful for the preparation of enzymatic liquid formulations having a defined enzymatic activity.

The consistency of the process was checked using different batches of cod viscera caught at different times of the year as starting material: the obtained fish proteases were confirmed to have a limited variability from batch to batch; this variability does not exceed the range of ±15% with respect to the obtained enzymatic activities.

The invention is illustrated in more detail in the following examples.

Example 1

Extraction of Crude Enzyme 52 kg of fish viscera was thawed overnight at room temperature, then combined with 103 L of a 20 mM calcium chloride dihydrate extraction buffer in a relative ratio of 1 kg of fish viscera: 2 L calcium chloride buffer. The resulting mixture (about 150 L) was adjusted to a final pH 7 value by addition of a sodium hydroxide water solution 50% w/v and stirred overnight at 4° C.

Large viscera chunks were separated by filtration with a net, leaving 130 L in the tank. 6.5 kg of diatomaceous earth (5% w/v) was added to the obtained mixture under stirring at room temperature, then filter pressed through 14 XE-400 filter sheets (7 cassettes). The filtered extract (100 L) was concentrated to 42 L using a 1×1 ultrafiltration spiral membrane (1 kDa cut off). The membrane was cleaned prior to concentrating with 100 L 0.1M sodium hydroxide water solution followed by reverse osmosis against water.

2 L of concentrated fish extract was removed for freeze drying, and the rest of the extract was stored at 4° C. until purification.

Example 2

Hydrophobic Interaction Chromatography (HIC) Purification

All purification steps were performed at 20-25° C. The concentrated fish extract was warmed to 20-25° C., and 58.82 g calcium chloride dihydrate was added. 4.93 kg of sodium acetate was added to obtain a 1.5 M concentration and the pH was adjusted to 8 using 5 M sodium hydroxide water solution.

The conductivity was checked to ensure that the correct concentration had been reached (adjusted to 56-60 mS; was 57.4 mS). After stirring for one hour, 0.8 kg of diatomaceous earth was added (2% w/v) and the obtained suspension was clarified by filter pressing through 4 XE-400 filter sheets (1 cassette). 40 L of feed material was obtained.

6 L of Capto-phenyl high sub column resin was conditioned with 20 L of 0.1M sodium hydroxide aqueous solution followed by 20 L reverse osmosis water.

Column pressure was maintained at 15 psi and a flow rate of 417 mL/minute. 40 L of 1.5 M sodium acetate at pH 8 was used to equilibrate the column. The eluates were also checked for conductivity (expected value 62 mS).

Primed feed was added to the column, washed with 15 L of equilibration buffer, then eluted with 20 L of a solution of 10% v/v glycerol and 5% v/v isopropanol (diluted with reverse osmosis water). Eluate was collected in 4 fractions, 5 L each, and the fractions with trypsin activity were pooled (15 L collected).

Example 3

Eluate Concentration, Dialysis, Freeze Drying

Concentrations and diafiltrations were performed using a cross tangential ultrafiltration unit with a 1 kDa membrane (Pall Filtron, USA). The selected eluates were concentrated to a final volume of 1.7 L. This solution was added with 1 L of 20 mM $CaCl_2$ water solution at pH 8 under stirring.

The resulting solution had 4.3% solids. Additional 1 L of $CaCl_2$ solution was added and the resulting solution showed 4.5% solids. The volume was reduced to 1.75 L by dialysis, then the concentrated and diafiltered eluate was freeze dried to afford 33 g of powder. The specific enzymatic activity of this powder was: Trypsin 240 U/mg, Chymotrypsin 5 U/mg and Collagenase 0.04 U/mg. The isolated enzyme exhibited several bands on SDS-PAGE: the main one, indicated with an arrow in FIG. 1, with an estimated molecular weight of 25,000.

Optionally the production process of fish proteases can be stopped after the dialysis step (i.e. avoiding the final freeze-drying step) to obtain fish proteases in aqueous solution at the desired concentration.

These solutions can be used for the preparation of final enzymatic formulations in phosphate-buffered saline solutions (PBS solutions) containing potassium chloride, potassium dihydrogen phosphate, sodium chloride, disodium monohydrogen phosphate, tetrasodium ethylenediaminetetraacetate and phenol red at a pH value comprise between 7.2 and 7.6.

These enzymatic formulations may contain 0.1-0.3 g/L of potassium chloride and potassium dihydrogen phosphate, 7-9 g/L of NaCl, 1.0-1.3 g/L of disodium monohydrogen phosphate, 2.4 mg/L of phenol red and sodium ethylenediaminetetraacetate at a final concentration ranging between 0.3 and 0.6 mM and include the Dulbecco's phosphate-buffered saline solution (Dulbecco, R et al. J. Exp. Med., 99, 167-182 (1954)).

Example 4

Analytical Characteristics of Fish Trypsin Purified According to the Invention

The characteristics of the fish trypsin isolated according to the invention are reported in the following Tables and in Figures.

Figure 2:
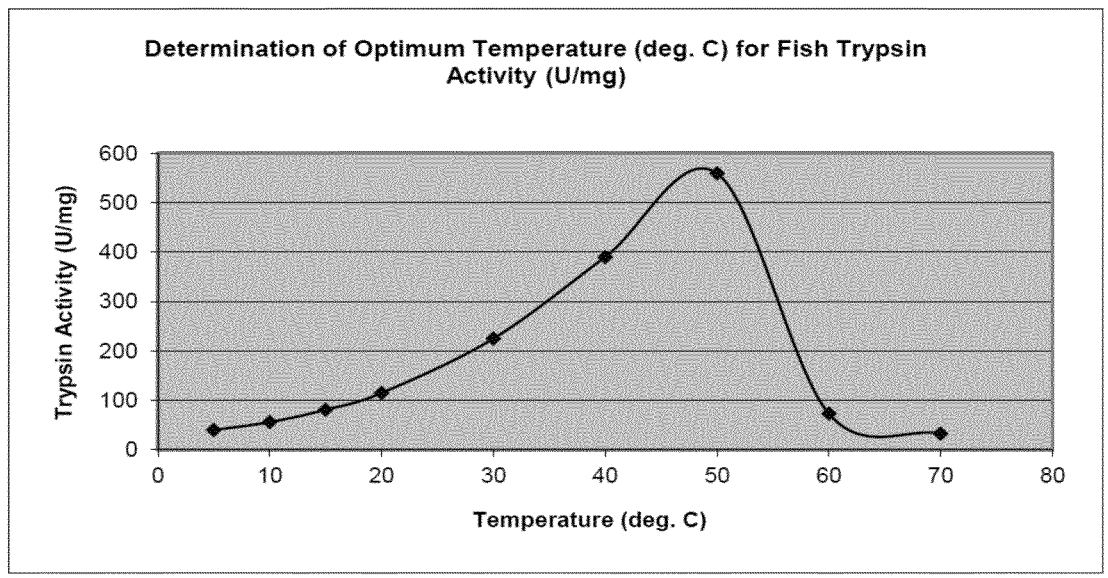

Optimum temperature range for enzymatic activity: Table 1 and FIG. 2 show the enzymatic activity of the prepared fish protease in the temperature range comprised between 5 and 70° C. Tested the main trypsin activity.

TABLE 1

| Temp. (deg. C.) | Trypsin Activity (U/mg) |
| --- | --- |
| 5 | 40 |
| 10 | 56 |
| 15 | 81 |
| 20 | 115 |
| 30 | 225 |
| 40 | 390 |
| 50 | 559 |
| 60 | 73 |
| 70 | 33 |

Figure 3:
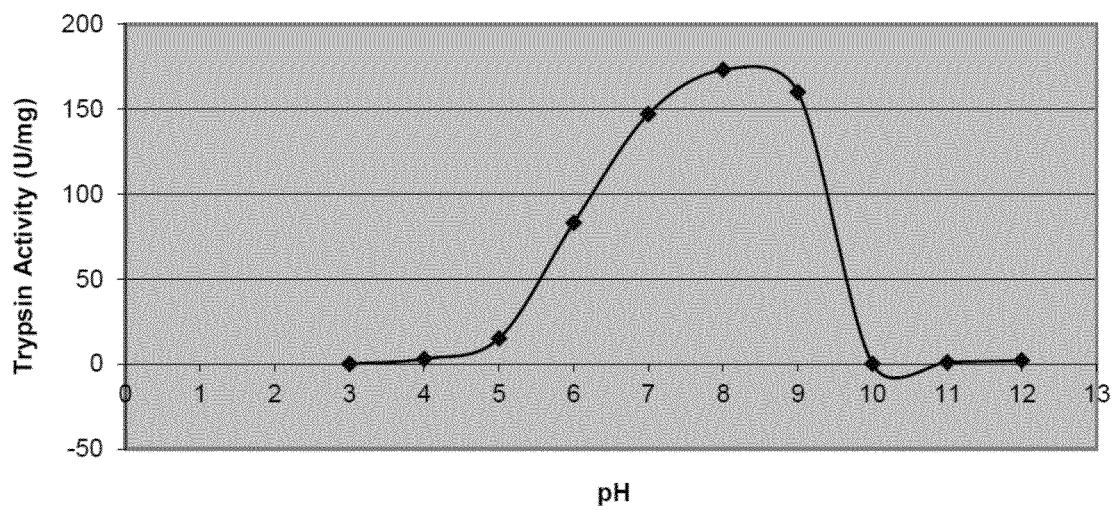

Optimum pH range for enzymatic activity: Table 2 and FIG. 3 show the enzymatic activity of the prepared fish trypsin in the pH range comprised between 3 and 12. The main trypsin activity has been tested.

TABLE 2

| pH | Trypsin Activity (U/mg) |
| --- | --- |
| 3 | 0 |
| 4 | 3 |
| 5 | 15 |
| 6 | 83 |
| 7 | 147 |
| 8 | 173 |
| 9 | 160 |
| 10 | 0 |
| 11 | 1 |
| 12 | 2 |

Figure 4:
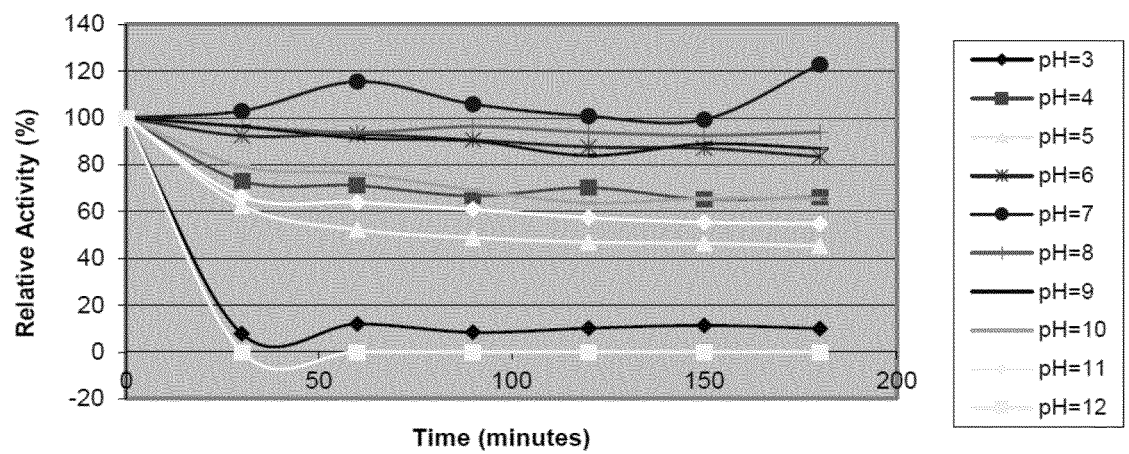

Stability data for the enzymatic activity over time at different pH values: Table 3 and FIG. 4 show the enzymatic activity of the prepared fish trypsin in the pH range of 3-10 in 3 hours at the temperature of 5° C. The same data of the Table 3 are presented in graphic form as relative enzymatic activity (100% of enzymatic activity at time zero; FIG. 4). The main trypsin activity has been tested.

TABLE 3

| | trypsin activity (U/mg) | | | | | | | |
| --- | --- | --- | --- | --- | --- | --- | --- | --- |
| time (minutes) | pH 3 | pH 4 | pH 5 | pH 6 | pH 7 | pH 8 | pH 9 | pH 10 |
| 0 | 168 | 205 | 205 | 169 | 136 | 161 | 161 | 168 |
| 30 | 13 | 171 | 128 | 156 | 140 | 155 | 155 | 133 |
| 60 | 13 | 157 | 107 | 157 | 157 | 151 | 147 | 128 |
| 90 | 20 | 157 | 100 | 153 | 144 | 155 | 145 | 116 |
| 120 | 14 | 148 | 96 | 148 | 137 | 151 | 135 | 107 |
| 150 | 17 | 171 | 95 | 147 | 135 | 149 | 143 | 110 |
| 180 | 19 | 165 | 93 | 141 | 167 | 151 | 140 | 110 |

Cell Culture: Biological "In Vivo" Tests

Figure 5:
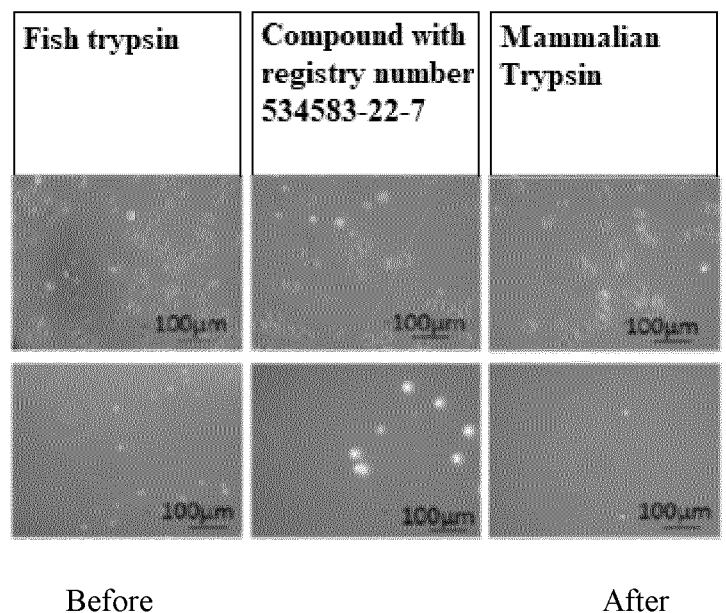

Comparative in vitro biological tests in PC12 cells, Human Glioma and Human Astrocyte were carried out using fish proteases prepared according to the process of the invention, compound with registry number 534583-22-7 and mammalian trypsin having approximately 3000 U/ml trypsin activity 0.25 w/v % Trypsin-1 mM EDTA/4Na Solution with Phenol Red (Wako, Japan 209-16941). Fish proteases prepared according to the invention recovered more PC12 cells than trypsin and the compound with registry number 534583-22-7 (Table 4). FIG. 5 shows the optical microscope observation of PC12 cell before and after treatment with Fish proteases prepared according to the claimed process, Accutase® and mammalian trypsin.

TABLE 4

Survival rate (%) of PC12 cells after treatment with treatment with Fish proteases prepared according to the claimed process, compound with registry number 534583-22-7 and Mammalian Trypsin. PC12 cells

| Enzyme | Number of recovered cells [×10^5 cells/well] | Ratio to Trypsin | Survival rate [%] |
|---|---|---|---|
| Fish proteases | 1.325 | 1.1 | 98.8 |
| Compound with registry number 534583-22-7 | 0.783 | 0.64 | 93.3 |
| Mammalian Trypsin | 1.22 | 1 | 97.3 |

The survival rate obtained with fish proteases prepared according to the claimed process is comparable to that obtainable with the compound with CAS registry number 534583-22-7 and to trypsin, depending on cell type; the best results with these fish proteases were obtained on PC12 cells (Table 5).

TABLE 5

Survival rate [%]

|  | PC12 cells | Human Glioma | Human Astrocytes |
|---|---|---|---|
| Fish proteases | 98.8 | 78.0 | 90.0 |
| Accutase ® | 93.3 | 83.4 | 91.3 |
| Mammalian Trypsin | 97.3 | 98.1 | 97.0 |

Further comparatives studies were carried out using the following cell lines: iPSC (induced pluripotent stem cells), NPC (neuronal progenitor cells) and U2OS (human bone osteosarcoma epithelial cells) in order to compare fish proteases obtained by process of the invention in comparison with mammalian trypsin having approximately 500-600 U/ml trypsin activity (Trypsin 0.05%/EDTA 0.53 mM 10× IN HBSS 1×, STERILE (Wisent Bioproducts, Quebec, Canada) and with the compound with CAS registry number 534583-22-7, with particular attention to the characteristics of cell attachment and viability and the final cell morphology.

For this purpose, 5,000 cells/well in 12 well plate were cultured for 5 days, starting the experiment when the it reached 70% confluency; then the medium was aspirated, rinsed with PBS and 0.5 mL of dissociation reagent was added and incubated at 37° C. for 3 minutes until dissociation (dissociation was monitored under the microscope until the optimal time was determined).

TABLE 6

Optimized incubation time of different enzymes for efficient dissociation on different cell lines

| Cell lines | Incubation time with Fish proteases | Incubation time with Trypsin | Incubation time with compound registry number 534583-22-7 |
|---|---|---|---|
| iPSC | 3 minutes | 3 minutes | 3 minutes |
| NPC | 3 minutes | 3 minutes | 3 minutes |
| U2OS | 14 minutes | 3 minutes | 3 minutes |

DMEM (Dulbecco's Modified Eagle Medium) was added to stop the enzyme reaction, then the cells were recovered by centrifugation at 1200 rpm for 3 min. The cells were re-suspended the in-culture medium; the cells number was determined by using lunar automated cell counter (Table 7). Treatment with fish proteases of the invention on iPSCs and NPCs did not affect cell attachment and viability as observed with trypsin.

TABLE 7

Cell numbers and viability of different cell lines after the enzymatic treatments

| Cell lines | test | Fish proteases | Mammalian Trypsin | Compound registry number 534583-22-7 |
|---|---|---|---|---|
| iPSC | Cell number | $0.5 \times 10^{-5}$ | $1.1 \times 10^{-5}$ | $2.95 \times 10^{-5}$ |
|  | Viability | 89.63% | 81.4% | 92.06% |
| NPC | Cell number | $0.52 \times 10^{-5}$ | $0.49 \times 10^{-5}$ | $0.39 \times 10^{-5}$ |
|  | Viability | 89.9% | 86.9% | 58.1% |
| U2OS | Cell number | $3.52 \times 10^{-5}$ | $2.1 \times 10^{-5}$ | $4.55 \times 10^{-5}$ |
|  | Viability | 95.1% | 100% | 96.8% |

Figure 6:
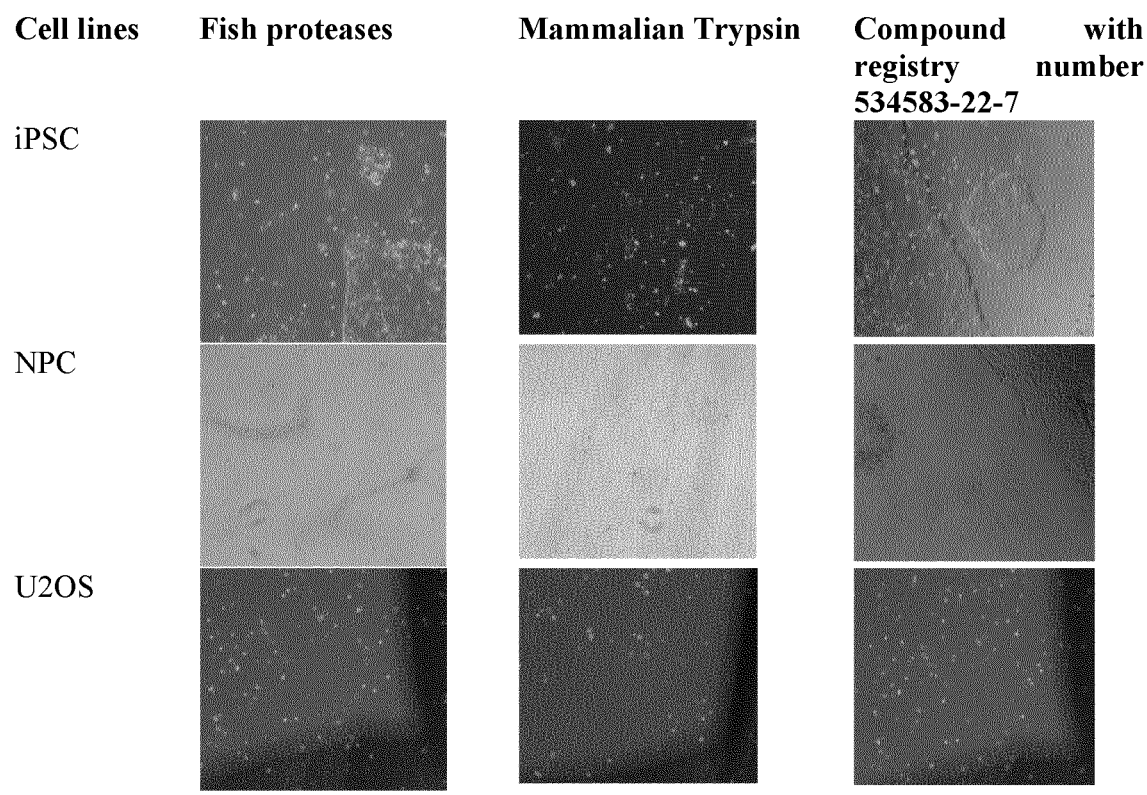

The cells were re-plated onto 12 well containing the medium and observed by optical microscopy after one week (FIG. 6). On the basis of this observations we confirmed that the cells treated with fish proteases of the invention did not change morphology and appeared healthy.

The purified fish proteases prepared according to the process of the invention present a peculiar enzymatic profile characterized by a trypsin activity of about 60-80% of the total enzymatic activity, collagenase activity being substantially negligible (Table 8).

TABLE 8

% of enzymatic activities of fish proteases obtained according to the process of the invention versus other commercially available proteases.

| | Compound with registry number 534583-22-7 (% of enzymatic activity) | AccuMax TM (% of enzymatic activity) | Accutase TM XL powder (% of enzymatic activity) | Fish proteases solution after diafiltration and freeze drying (% of enzymatic activity) |
|---|---|---|---|---|
| Trypsin activity | 29 | 49 | 26 | 78.0 |
| Chymotrypsin activity | 0 | 0 | 0 | 1.6 |
| Collagenase type I activity | 59 | 47 | 67 | 0.01 |
| Protease activity | 12 | 5 | 7 | 21.0 |

The invention claimed is:

1. Fish proteases isolated from cod fish viscera comprising an average specific Trypsin activity of 240±40 U/mg, Chymotrypsin activity of 4±2 U/mg, Collagenase activity of 0.04±0.02 U/mg and a Protease activity of 65±10 U/mg obtained by a process comprising:
   a) extracting crude enzyme from the cod fish viscera with a calcium chloride buffer at pH 7, filtrating and ultrafiltrating to obtain an ultrafiltrate;
   b) extracting the ultrafiltrate with an aqueous solution of CaCl2 having conductivity from 52 to 62 mS in a pH range of 7.2 to 8.2 followed by depth filtration to obtain a filtrate;
   c) purifying by hydrophobic interaction chromatography the filtrate obtained in step b) using as stationary phases an agarose base matrix with straight chain alkyl ligands or aryl ligands, and eluting with buffers of low salt content and then with an aqueous mixture of water miscible organic solvents and a polyol to obtain a purified fraction with trypsin activity;
   d) dialyzing the purified fraction obtained from step c); and
   e) freeze-drying the dialysate from step d) to obtained the fish proteases.

2. The fish proteases according to claim 1, wherein step a) is carried out at a temperature between 4 and 25° C.

3. The fish proteases according to claim 1, wherein the calcium chloride in step a) is at a final concentration of 20 mM.

4. The fish proteases according to claim 1, wherein the ultrafiltrating step a) is carried out using a membrane with a 1 kDalton cut off.

5. The fish proteases according to claim 1, wherein the agarose base matrix of the stationary phase used in step c) comprises aryl ligands and a particle size distribution between 50 and 100 microns.

6. The fish proteases according to claim 1, wherein the chromatographic elution with buffers of low salt content in step c) is done using a 1.5 M aqueous sodium acetate solution.

7. The fish proteases according to claim 1, wherein the water miscible organic solvent utilized in the chromatographic elution in step c) is isopropanol.

8. The fish proteases according to claim 1, wherein the polyol utilized as component of the chromatographic elution in step c) is glycerol.

9. The fish proteases according to claim 1, wherein step c) is carried out at a temperature between 4 and 25° C.

* * * * *